United States Patent [19]

Kushner et al.

[11] 4,152,070
[45] May 1, 1979

[54] TURBIDIMETER

[75] Inventors: Jack Kushner, Lindenhurst; Henry G. Zwirblis, Nesconset, both of N.Y.

[73] Assignee: Envirotech Corporation, Menlo Park, Calif.

[21] Appl. No.: 765,651

[22] Filed: Feb. 4, 1977

[51] Int. Cl.² ............... G01N 21/06; G01N 21/22; G01N 21/26
[52] U.S. Cl. ................................. 356/343; 250/574; 356/442
[58] Field of Search ............... 356/206, 208, 104; 250/573, 574; 350/172

[56] References Cited
U.S. PATENT DOCUMENTS

| 3,515,482 | 6/1970 | Garrow et al. | 356/103 |
| 3,522,436 | 8/1970 | Posgate | 356/104 UX |
| 3,666,359 | 5/1972 | Lee | 356/71 |
| 3,785,735 | 1/1974 | Friedman et al. | 356/39 |
| 3,788,744 | 1/1974 | Friedman et al. | 356/104 X |
| 3,850,525 | 11/1974 | Kaye | 356/73 |
| 4,043,669 | 8/1977 | Gehatia et al. | 356/104 |

OTHER PUBLICATIONS
Electronics, Dec. 20, 1973, pp. 30 and 31.

Primary Examiner—Vincent P. McGraw
Assistant Examiner—Rodney B. Bovernick
Attorney, Agent, or Firm—Michael J. Pollock; Robert E. Krebs

[57] ABSTRACT

A turbidimeter for measuring the turbidity of a sample of fluid comprises a transparent sample cell, a light source for directing a beam of light through the sample cell, and beam separating means comprising a hollow tube and reflective means encompassing the tube. The hollow tube is positioned for receiving unscattered light transmitted through the sample cell and transmitting it to a light responsive detector. The reflective means is positioned and oriented for receiving light scattered by the fluid in the sample cell and directing it to a second light responsive detector. A comparison of the outputs of the two detectors provides a measure of the turbidity of the sampled fluid. This arrangement is compact, economical and shock-resistant, and it provides a measure of turbidity which is relatively unaffected by changes in color, the accumulation of turbid films on the sample cell wall and variations in the intensity of the light source.

7 Claims, 3 Drawing Figures

TURBIDIMETER

BACKGROUND OF THE INVENTION

There is a steadily increasing need for economical and reliable apparatus to measure the turbidity of fluid samples. Turbidity, which denotes the tendency of a sample to scatter and absorb light rather than transmit it, has become a commonly accepted criterion of water quality. Turbidity is typically caused by the presence of suspended matter such as clay, mud, algae, rust, bacteria, and calcium carbonate. Many processes for the treatment of water for potable or industrial usage depend upon turbidimeters for efficient and economical operation. For example, turbidimeters are used to automatically control chemical dosage rates and to monitor the effluent from a filter. With increasing emphasis on pollution control, the need for economical and reliable turbidimeters has increased substantially in recent years.

While a variety of complex optical systems have been used to measure turbidity in a carefully controlled laboratory environment, many of these optical systems are too delicate for reliable field operation. Turbidimeters for field use, particularly for prolonged use in installations for automatic control, are typically subject to shock in transport, changes in the color of the fluid sampled, the buildup of turbid films on the sample cell, and variations in the intensity of the light source.

SUMMARY OF THE INVENTION

In accordance with the present invention, a turbidimeter for measuring the turbidity of a sample of fluid comprises a transparent sample cell, a light source for directing a beam of light through the sample cell, and beam separating means comprising a hollow tube and reflective means encompassing the tube. The hollow tube is positioned for receiving unscattered light transmitted through the sample cell and transmitting it to a light responsive detector. The reflective means is positioned and oriented for receiving light scattered by the fluid in the sample cell and directing it to a second light responsive detector. A comparison of the outputs of the two detectors provides a measure of the turbidity of the sampled fluid. This arrangement is compact, economical and shock-resistant, and it provides a measure of turbidity which is relatively unaffected by changes in color, the accumulation of turbid films on the sample cell wall, and variations in the intensity of the light source.

BRIEF DESCRIPTION OF THE DRAWINGS

The advantages, the nature and various additional features of the present invention will appear more fully upon consideration of the illustrative embodiments now to be described in detail in connection with the accompanying drawings in which.

For convenience of reference, the same reference numerals are used to designate the same elements throughout the drawing.

DETAILED DESCRIPTION

Figure 1:
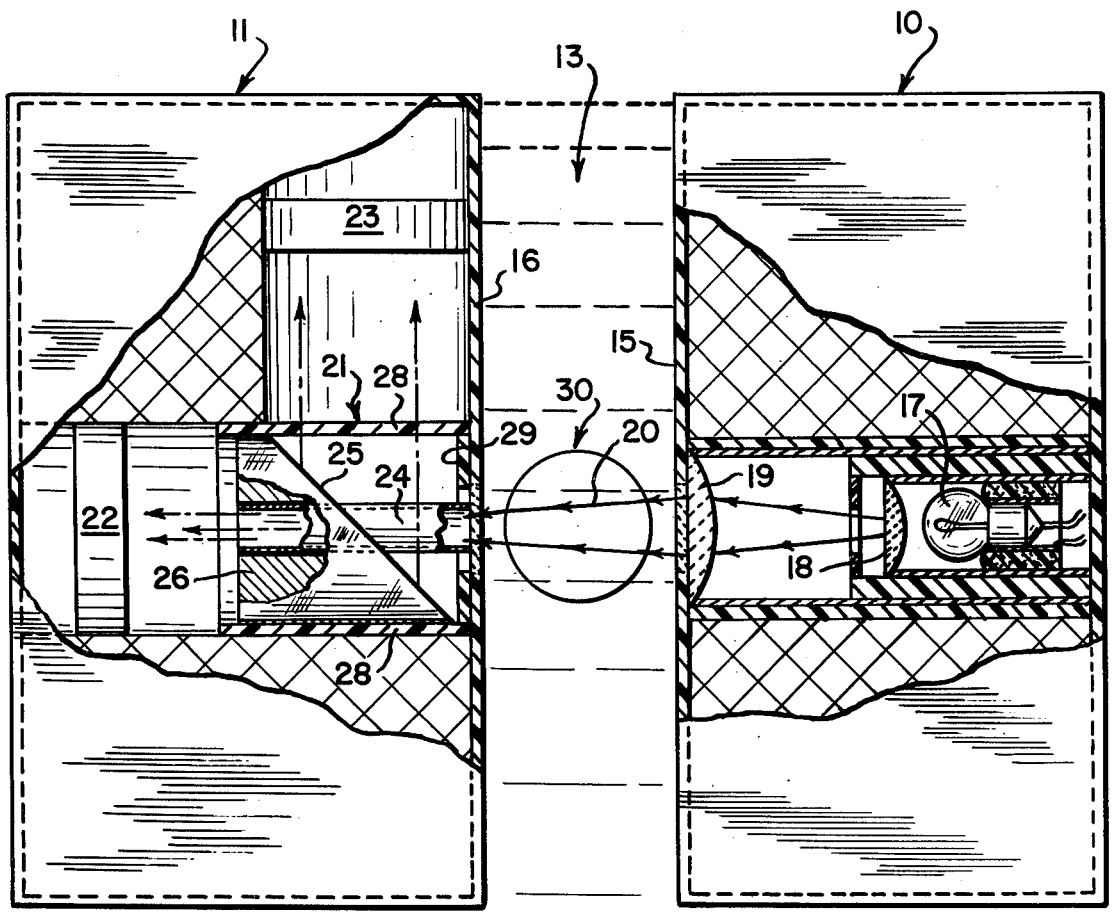
FIG. 1 is a schematic side view of a preferred embodiment of a turbidimeter in accordance with the invention.

Referring to the drawings, FIG. 1 is a schematic view of a preferred embodiment of a turbidimeter comprising a light beam unit 10, a beam analyzer unit 11, and a sample space 13 for fluid therebetween. While the two units and the sample space can optionally be in the form of a single unit which includes a sample cell, in the preferred embodiment illustrated the light beam unit and the beam analyzer unit are separate sealed units sealed by water-tight walls 15 and 16, respectively. The units are optically aligned and spaced apart within the fluid to be analyzed thereby defining a sample space in the region between them.

Light beam unit 10 is a source for providing a beam of light aligned to pass through the sample fluid into the beam analyzer unit. In the preferred embodiment, it comprises a light source 17, and a pair of aspheric collimating lenses 18 and 19 for directing a beam of light 20 through a transparent portion of wall 15, through the sample space 13, and into beam analyzer unit 11.

Beam analyzer unit 11 comprises a beam splitter 21 for separating light transmitted with the beam from light scattered from the beam, photosensitive detectors 22 and 23 for receiving transmitted and scattered light, respectively, and producing respective outputs representative of the relative levels of the transmitted and scattered light. Calibration circuitry, such as a simple bridge circuit (not shown) can be used to compare the outputs of detectors 22 and 23, and thereby provide a calibratable measure of turbidity.

Figure 2:
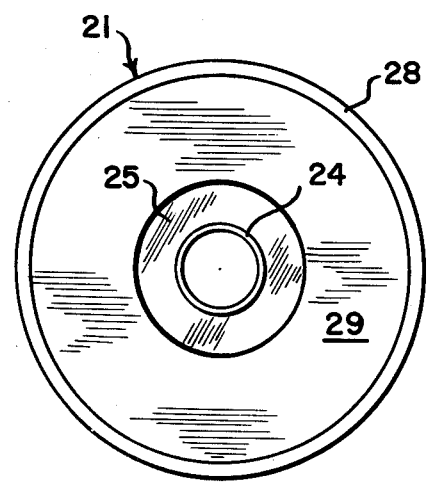
FIG. 2 is an end view of the beam separator used in FIG. 1.

Beam splitter 21 schematically shown in FIG. 1, and shown in end view in FIG. 2, comprises a light guide 24 having a light aperture and light impermeable walls for selectively receiving light transmitted with the beam and permitting the passage of such light within the walls along an optical path to photosensitive detector 22. Preferably, such guide is an elongated, thin-walled, hollow tube which can have substantially the same transverse cross-sectional shape and area as that of beam 20. The inner walls of the guide are preferably light reflecting. The tube is positioned and oriented so that one open end is in position for receiving the transmitted beam 20, and the other open end is aligned with photosensitive detector 22. Substantially surrounding tube 24 is a reflecting surface 25 for directing scattered light along an optical path to a second photosensitive detector. For example, the reflecting surface can be a planar surface which is inclined with respect to the axis of beam 20 so that scattered light which fails to enter light guide 24 is reflected onto photosensitive detector 23. In the preferred embodiment, the reflecting surface is formed, as by polishing, on a solid substrate 26, which can be aluminum. Tube 24 passes through the substrate and can be integrally bonded thereto. The substrate in turn can be integrally bonded within a cylindrical wall of transparent plastic 28, and the entrance end of the wall can be provided with a restricted area opaque entrance diaphragm 29 for reducing the entry of stray light.

In some applications, it is required to also take readings of the intensity of the light scattered at 90° with respect to beam 20. Accordingly, an optional third photosensitive element 30 is shown so disposed. This element can be switched into the circuitry in place of element 23, when 90° sensing is required.

In operation of the device, light from source 17 is collimated by lenses 18 and 19 into a beam 20. The transmitted portion of the beam passes through a fluid sample disposed between walls 15 and 16, and into tube 24, through which it passes to photosensitive detector 22. The portion of the beam which is scattered by the fluid sample deviates from the beam axis and, for typical sampling distances, the bulk of this scattered portion spreads beyond the entrance to tube 24 and falls upon reflecting surface 25, whereupon it is reflected onto photosensitive detector 23. The incidence of light on detectors 22 and 23 produces respective electrical output signals representative of the intensity of incident light, and a comparison of the ratio of these output signals provides a calibratable measure of the turbidity of the fluid sample.

In tests using a 15.5 millimeter diameter cylindrical diaphragm and 28 millimeter sample distance, the following calibration readings were observed, where C is the concentration of impurities in a water sample in parts per million by weight and $S_2/S_1$ is the ratio of the scattered light detector output signal to the transmitted light output signal:

| C | $S_2/S_1$ |
| --- | --- |
| 2 | 0.0102 |
| 4 | 0.0109 |
| 6 | 0.0117 |
| 8 | 0.01238 |
| 10 | 0.0132 |
| 20 | 0.01815 |
| 30 | 0.02459 |
| 40 | 0.0342 |
| 50 | 0.040 |
| 130 | 0.093 |
| 230 | 0.1259 |
| 280 | 0.1528 |
| 610 | 0.3518 |
| 750 | 0.368 |
| 780 | 0.4545 |
| 950 | 0.47368 |

Figure 3:
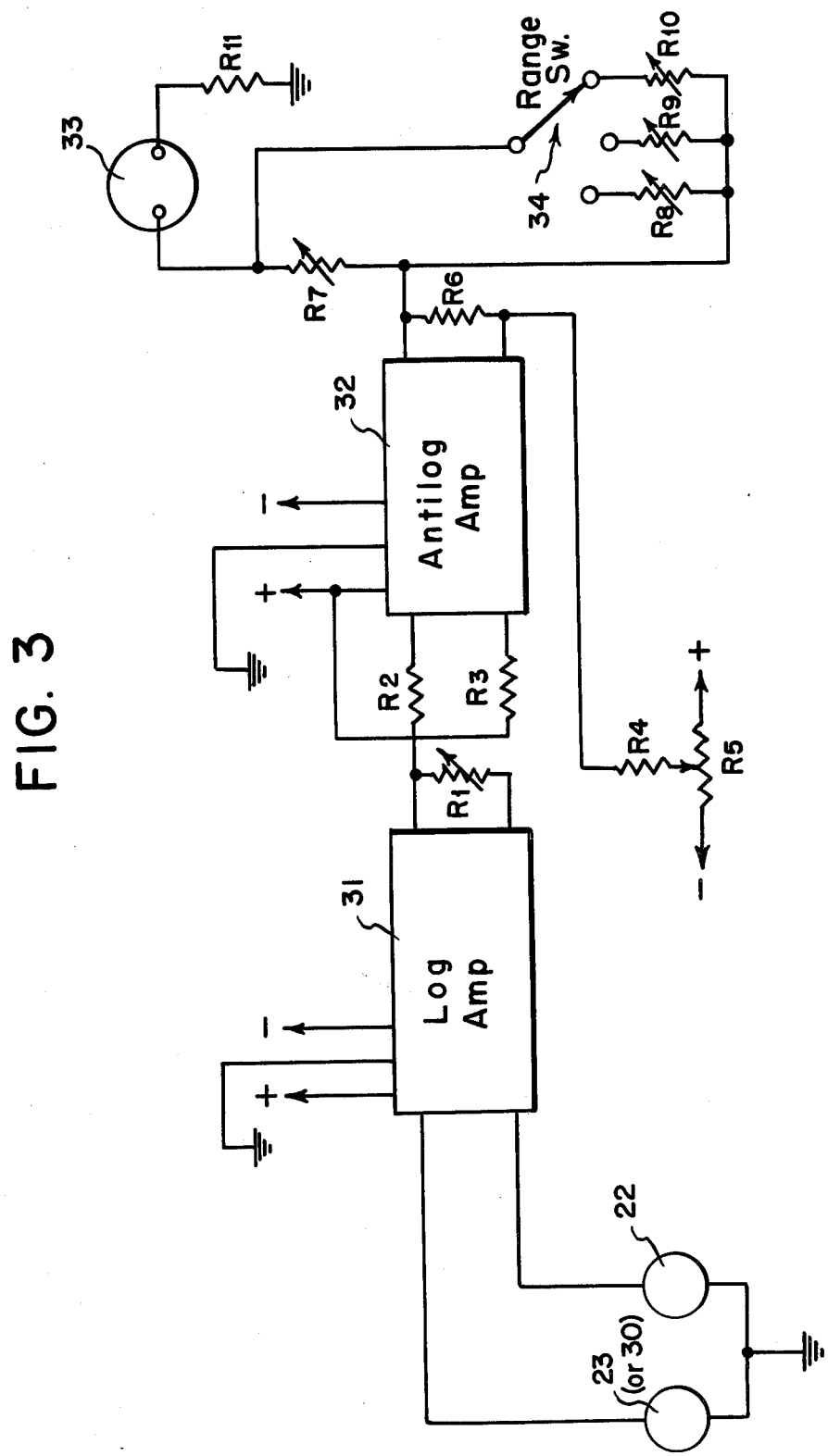
FIG. 3 illustrates circuitry useful in the device of FIG. 1.

FIG. 3 illustrates preferred electronic circuitry for use with a turbidimeter in accordance with the invention. This circuitry, in substance, comprises electronic processing means for processing the outputs of photocells 22 and 23 or 30 in accordance with a "best-fit" equation relating the concentration of impurities to the respective photocell outputs. One example of such an equation is:

C proportional to antilog [K log (X/Y)+C]

wherein C is the impurity concentration, X is the output of photocell 22, and Y is the output of photocell 23 or 30.

As shown, the outputs of photocells 22 and 23, which can be a matched pair of International Rectifier 48–1226 Photocells, are applied to the input terminals of logarithmic amplifier 31. The output, which represents log (X/Y), is effectively multiplied by the constant K through variable resistor $R_1$. The K log (X/Y) signal is applied to one input terminal of an antilogarithmic amplifier 32, and a reference signal representative of the constant C is applied to the other input terminal through resistor $R_3$. The two amplifiers can be logarithmic and antilogarithmic Burr-Brown 4127 amplifiers respectively.

The output of antilog amplifier 32, which is linearly proportional to concentration, is properly zeroed by a reference signal applied through resistors $R_4$ and $R_5$, and applied to calibration circuitry wherein it is displayed on microammeter 33. The amplifiers and reference signals are conveniently supplied by a 15-volt D.C. power source (not shown), and the calibration circuitry can be provided with a range switch 34 and an adjustable resistor $R_7$ for fine adjustment in accordance with principles well known in the art.

The advantages of this device are manifold. Because the beam splitter is a simple substantially unitary structure, the device is economical to manufacture and ruggedly resistant to shock and vibration. Because the device measures the ratio between scattered and transmitted light which have nearly identical light paths, its accuracy is relatively unaffected by changes in color, accumulations of turbid films on the walls adjacent the fluid sample, or variations in the intensity of the light source. Thus, the invention provides a turbidimeter particularly suitable for use in prolonged remote monitoring which can be submerged in a tank stream or lake and connected to control circuitry by a simple cable.

While the invention has been described in connection with only a small number of specific embodiments, it is to be understood that these are merely illustrative of many other specific embodiments which also utilize the principles of the invention. Thus, numerous and varied devices can be made by those skilled in the art without departing from the spirit and scope of the present invention.

We claim:

1. Apparatus for measuring the turbidity of a sample of fluid comprising:
    a light source for directing a beam of light through a sample space for containing a sample fluid into a beam splitter;
    first and second photosensitive detecting means for receiving light and producing an electrical output indicative of the intensity of received light;
    a beam splitter for receiving light from said source and separating light transmitted with said beam from light scattered from said beam, said beam splitter comprising:
    (1) light guide means having a light aperture and light impermeable walls for selectively receiving through said aperture light transmitted with said beam and permitting the passage of said light within said walls along a first optical path to said first photosensitive detector and (2) reflecting means substantially surrounding said light guide for directing light scattered from said beam along a second optical path to said second photosensitive detecting means;
    and electrical circuit means responsive to the electrical outputs of said photosensitive detecting means for producing an electrical output indicative of the turbidity of fluid disposed in said sample space.

2. Apparatus according to claim 1 wherein the inner walls of said light guide means are light reflecting.

3. Apparatus according to claim 1 wherein said light guide means comprises a tubular member.

4. Apparatus according to claim 1 wherein said light guide comprises a hollow tube having an aperture which is substantially the same shape and area as that of said light beam.

5. Apparatus according to claim 1 wherein said reflecting means comprises a planar reflecting surface which is positioned and oriented to be inclined with respect to the axis of said beam.

6. Apparatus according to claim 1 wherein:

said light guide comprises a tubular member having a light aperture which is substantially the same shape and area as that of said light beam; and said reflecting means comprises a planar reflecting surface substantially surrounding said tubular member which planar surface is inclined with respect to the axis of said beam.

7. Apparatus according to claim 6 wherein said reflecting surface is formed on a solid substrate and said tubular member is integrally connected to said substrate.

* * * * *